United States Patent [19]
Hirai et al.

[11] Patent Number: 5,059,542
[45] Date of Patent: Oct. 22, 1991

[54] ARTIFICIAL CARRIER PARTICLES AND METHOD FOR PREPARATION THEREOF

[75] Inventors: Takenori Hirai; Hirotaka Ihara; Chuichi Hirayama; Haruo Fuzita; Munehiro Saisho, all of Kumamoto, Japan

[73] Assignee: Juridical Foundation the Chemo-sero-Therapeutic Research Institute, Kumamoto, Japan

[21] Appl. No.: 420,531

[22] Filed: Oct. 12, 1989

[30] Foreign Application Priority Data

Oct. 12, 1988 [JP] Japan .................................. 63-258004

[51] Int. Cl.$^5$ .......................................... G01N 33/543
[52] U.S. Cl. .................................... 436/518; 436/534; 525/54.1; 525/54.2
[58] Field of Search ........................ 525/54.1, 54.2; 436/518, 534

[56] References Cited

U.S. PATENT DOCUMENTS

| | | | |
|---|---|---|---|
| 4,276,206 | 6/1981 | Katz | 525/54.1 |
| 4,342,739 | 8/1982 | Kakimi et al. | 436/518 |
| 4,416,813 | 11/1983 | Ikeda et al. | 436/529 |
| 4,935,465 | 6/1990 | Garman | 525/54.1 |

FOREIGN PATENT DOCUMENTS

0001728 1/1987 Japan .

OTHER PUBLICATIONS

Hirayama et al., *Chemical Abstracts* 106:157696m, Abstract of JP-1,728, (1987).

*Primary Examiner*—Richard L. Raymond
*Assistant Examiner*—Mark W. Russell
*Attorney, Agent, or Firm*—Fleit, Jacobson, Cohn, Price, Holman & Stern

[57] ABSTRACT

An artificial carrier particle comprising an anionic polymer and a synthetic polyamino acid having at least one carboxylic group and at least one amino group in its side chain, the complex being insolubilized by an aldehyde crosslinking agent. The artificial carrier particle is useful in immunoassay, in particular, particle immunoassay. The artificial carrier particles are obtained by preparing an aqueous solution containing an anionic polymer and a synthetic polyamino acid comprising at least one free carboxyl group and at least one free amino group in its side chain, adjusting the pH of the solution to 3.5 to 9.5 at room temperature or at progressively increasing temperature under stirring to form solution particles of a desired particle size, and insolubilizing the particles by an aldehyde crosslinking agent.

8 Claims, 5 Drawing Sheets

ARTIFICIAL CARRIER PARTICLES AND METHOD FOR PREPARATION THEREOF

BACKGROUND OF THE INVENTION

The present invention relates to novel artificial particles useful as carriers for immunoassay, in particular, particle immunoassay, to preparation thereof and to immunoassay reagent comprising the particles.

The method for particle immunoassay is based on the steps of using particles of appropriate size as carriers, adsorbing antigens or antibodies onto the carriers and observing the agglutination of the thus sensitized carriers caused by antibodies or antigens corresponding thereto.

Examples of the most popular carriers conventionally used in particle immunoassay include erythrocytes of various animals such as sheep and chicken, and artificial synthetic polymer particles such as polystyrene latex particles. Although the former method in which the erythrocytes of animals are used as the carriers has been known as one utilizing so-called hemagglutination, this method has advantages in that it can be applied to many kinds of antigens and antibodies and, for example, the immunoassay can be finished in a short time (1 to 2 hours) by employing the microtiter method. However, there are disadvantages in that the erythrocytes per se have inherent antigenecity so that non-specific agglutination arises easily, and that differences in the properties of the erythrocytes depending on the individual, season and the like are very large and the erythrocytes cannot be obtained in a uniform quality since they are collected from living animals. Furthermore, although there is an advantage in that the size of the erythrocytes is constant for a given kind of animal, this causes a disadvantage in that there cannot be obtained particles having a desired size in accordance with the purpose of use.

On the other hand, synthetic polymer particles such as polystyrene latex generally have a particle diameter of about $0.1 \sim 1$ $\mu$m and the particles are particularly useful as carriers for agglutination reaction. The particles have advantages in that the particles per se have no antigenecity and can be constantly obtained in a uniform quality and in a large amount. However, in the case where the microtiter method is used in order to obtain a high sensitivity and to conduct quantitative analysis, the carriers consisting of the conventional synthetic polymer particles have a problem in that a long time period is required for sedimentation, compared with the case of using erythrocytes as carriers and, therefore, the assay cannot be rapidly finished. In addition, there is a possibility of natural agglutination, i.e., non-specific agglutination, occurring in the natural PH region preferably for a immunoreaction medium.

Although it is known that natural inorganic particles such as kaolin and carbon powder are useful as the carriers mentioned above, these particles have disadvantages in that the antibodies or antigens are difficult to sensitize to a high degree and cannot easily be selected in a constant particle range, and therefore, the particles can only be used in an extremely limited field.

Furthermore, there has recently been developed an artificial carrier comprising gelatin, water soluble polysaccharides and sodium polymethacrylate and being crosslinked by an aldehyde crosslinking agent (see Japanese Patent Un-examined Publication Nos. 57-153658 and 57-160465) and this carrier is being put to use as a carrier consisting of gelatin particles instead of animal erythrocytes. The above mentioned Japanese Patent Un-examined Publications disclose that the artificial particles have properties similar to those of animal erythrocytes, which are the best conventional carriers for immunoagglutination reaction, are also chemically and physically stable, have no antigenecity, and can be easily prepared in a desired particle size in a large amount.

However, gelatin is a natural protein material and its properties change depending on the raw material thereof so that the particles cannot always be prepared with uniform properties. Further, the trend toward greater speed and automation in the field of clinical analysis makes it desirable to be able to carry out the reaction in the agglutination reaction analysis more rapidly than possible using animal erythrocytes or gelatin particles.

Therefore, the present invention aims to provide novel carrier particles which are more uniform and stable and enable the agglutination reaction to be carried out more rapidly, compared with the conventional carriers. The carrier particles of the present invention are prepared from a starting material which is not a natural material but a synthetic material, i.e., polyamino acid, where the coacervation method is used as a granulation method.

Contrary to gelatin, the polyamino acid used in the present invention does not gelatinize at room temperature in the granulation process, so that it is possible to prepare coacervate particles. In this method, it is unnecessary to cool the system at the time of making the particles insoluble and also unnecessary to control the temperature of the system, since the speed of the reaction between the particles and the crosslinking agent is slow.

It is suggested in Japanese Patent Un-examined Publication No. 55-94636 that synthetic polyamino acid be used as carrier particles for antigen-antibody reaction. The publication relates to a microcapsule for use in antigen-antibody reaction obtained by the coacervation microcapsule technique and discloses on page 5 line 2 from the bottom that polyamino acid resin is usable as a material capable of forming a capsule shell. However, this prior art substantially discloses gelatin-gum arabic capsule particles, the core of which is formed from oily material and does not specifically disclose any method for preparing capsule particles by using a particular polyamino acid under particular conditions. In fact, experiments conducted by the present inventors revealed that it was very difficult to obtain particles using a commercially available polyamino acid, for example, poly-L-glutamic acid, under coacervation.

Furthermore, Japanese Patent Un-examined Publication No. 62-1728 discloses a polyamino acid spherical particle and a method for preparation thereof and also discloses that one of its uses is as a latex for bioreaction. However, since the particles are prepared by dissolving hydrophobic polyamino acid in an organic solvent and dispersing the thus prepared solution into aqueous medium which is a non-solvent, the thus-prepared particles are essentially hydrophobic and have disadvantages similar to those of polystyrene latex. In addition, as is clear from the Examples set out in the specification, the spherical particles prepared by this conventional method are of a particle diameter of about $40 \sim 75$ $\mu$m or $75 \sim 200$ $\mu$m and it has been confirmed that even when particles of not more than 10 $\mu$m are obtained by sieving the thus obtained particles are not true spheres and do not sufficiently sensitize the antigens and antibodies.

SUMMARY OF THE INVENTION

It is therefore a primary object of the present invention to provide improved artificial carrier particles which overcome the disadvantages of the conventional carrier particles for particle immunoassay, in particular, carrier particles which are chemically and physically stable and which are capable of producing results in a short time period in an assay such as a microplate agglutination reaction.

Other objects of the present invention will be clear from the following description.

The primary and other objects can be attained by forming particles of complex comprising synthetic polyamino acid having at least one carboxyl group and at least one amino group in its side chain and an anionic polymer by phase separation, i.e., coacervation, and insolubilizing the resulting particles utilizing a cross-linking agent so as to obtain artificial particles. In more detail, the artificial carrier particles of this invention can be obtained by preparing a synthetic polyamino acid having at least one carboxyl group and at least one amino group in its side chain in an appropriate ratio as described later, forming liquid drops (coacervate) of small size from the polyamino acid and a water soluble anionic polymer according to the complex coacervation method and insolubilizing the drops. In this regard, there can be obtained carrier particles having a desired particle diameter and sensitivity by appropriately controlling the ratio of the carboxyl group and the amino group present in the polyamino acid as the raw material, the mixing ratio of the polyamino acid and the anionic polymer, and the coacervation paramaters, for example, the pH.

DESCRIPTION OF THE PREFERRED EMBODIMENTS

Although the polyamino acid having at least one carboxyl group and at least one amino group in its side chain usable in this invention can be prepared by any method known in the art, one of the following three methods is generally preferable. In this connection, polyamino acid used as a raw material and the method for preparation thereof are well known and therefore, any of various kinds of the polymers and methods for preparation thereof can be selected in accordance with the purpose.

(1) Introduction of amino group into acidic polyamino acid having the following formula:

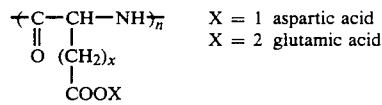

X = 1 aspartic acid
X = 2 glutamic acid

Figure 1:
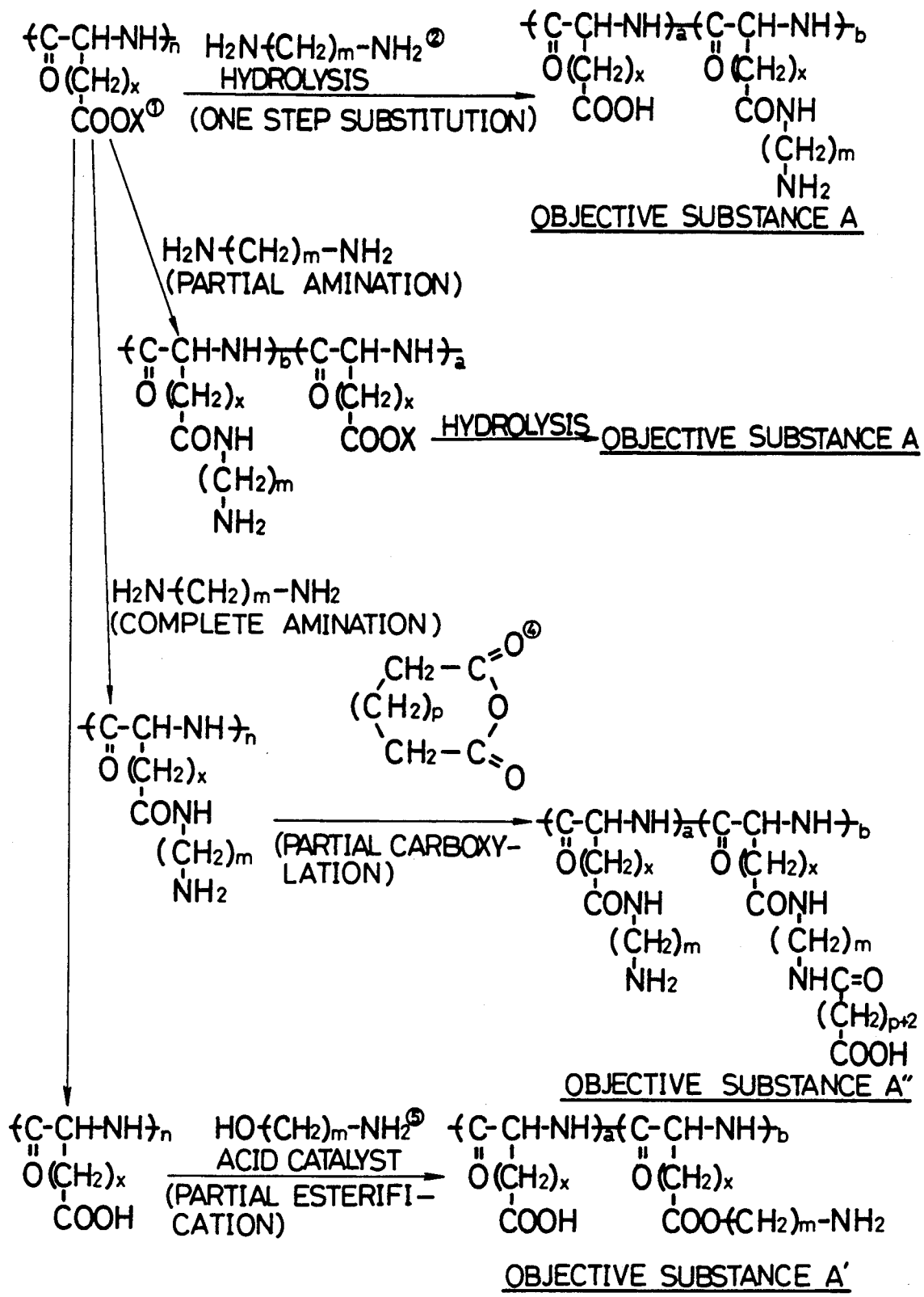
FIG. 1 represents reaction equations by which synthetic polyamino acids of the present invention having at least one carboxyl group and at least one amino group are prepared.

As shown by the reaction equations of FIG. 1, the amino group is introduced into the polyamino acid via COOX group thereof by use of polyamine or amino alcohol having a valency of not less than two. The marks ① to ⑥ have the following meanings:

① X generally represents a protective group and usually represents methyl, ethyl or benzyl group.

② Although divalent aliphatic amine is shown (m=2,3,4,6...), for convenience, an aryl amine such as phenylene diamine, polyamine having a valency of not less than three, or the like, can be used insofar as the introduction of the amino group can be accomplished for the purpose of the present invention.

③ Hydrolysis is carried out to eliminate the protective group. In this case, an alkali such as NaOH and KOH is ordinarily used.

④ P is zero or 1. Alternatively, the following compound or the like can be used.

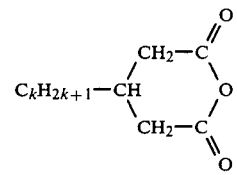

⑤ Although an aliphatic alcohol (m=2,3,4,6,...) is shown, an aryl alcohol or the like can be used.

⑥ p-toluene sulphonic acid, HCl or the like can be used as an acid catalyst.

(2) Introduction of COOH group into basic polyamino acid having the following formula:

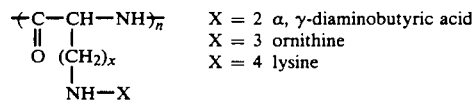

X = 2 α, γ-diaminobutyric acid
X = 3 ornithine
X = 4 lysine

Figure 2:
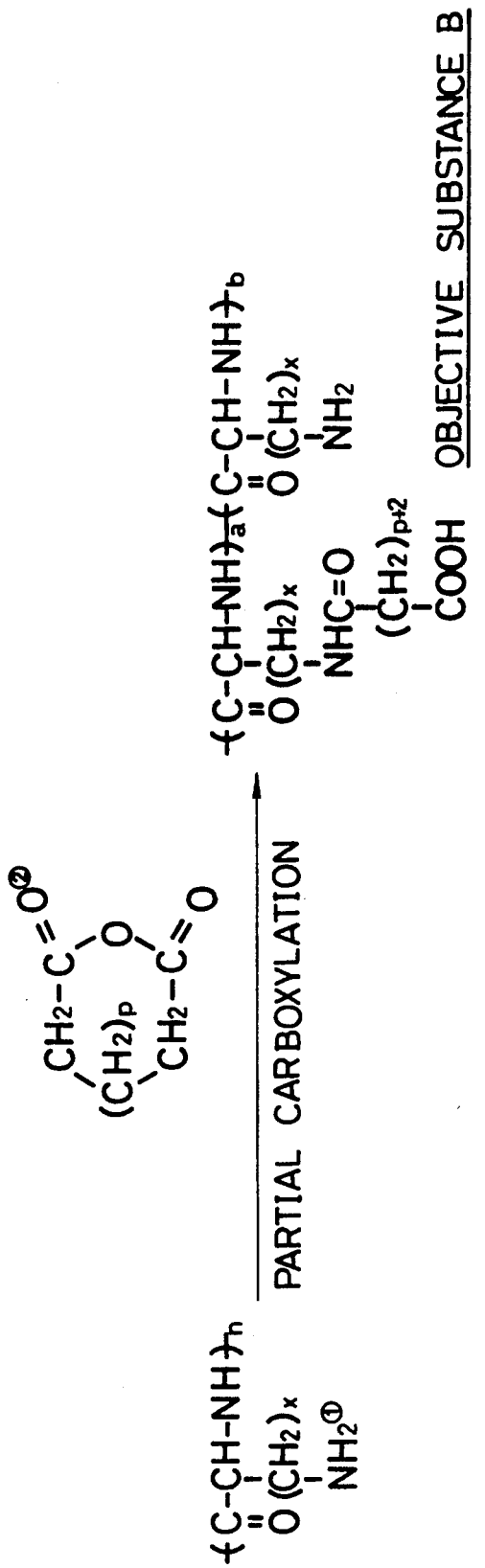
FIG. 2 represents another reaction equation by which a synthetic polyamino acid of the present invention having at least one carboxyl group and at least one amino group is prepared.

As shown by the reaction equation of FIG. 2, COOH group is introduced into the polyamino acid via NH$_2$ group thereof by use of an acid anhydride. The marks ① to ② have the following meanings:

① The compound after eliminating the protective group is shown. As a rule, NH$_2$ group of basic polyamino acid is protected by carbobenzoxy (Cbz), P-chlorocarboxybenzoxy (Clz) or the like during the synthesis. The elimination of the protective group can be carried out by the conventional method.

② is the same as ④ of (1) mentioned above.

Figure 3:
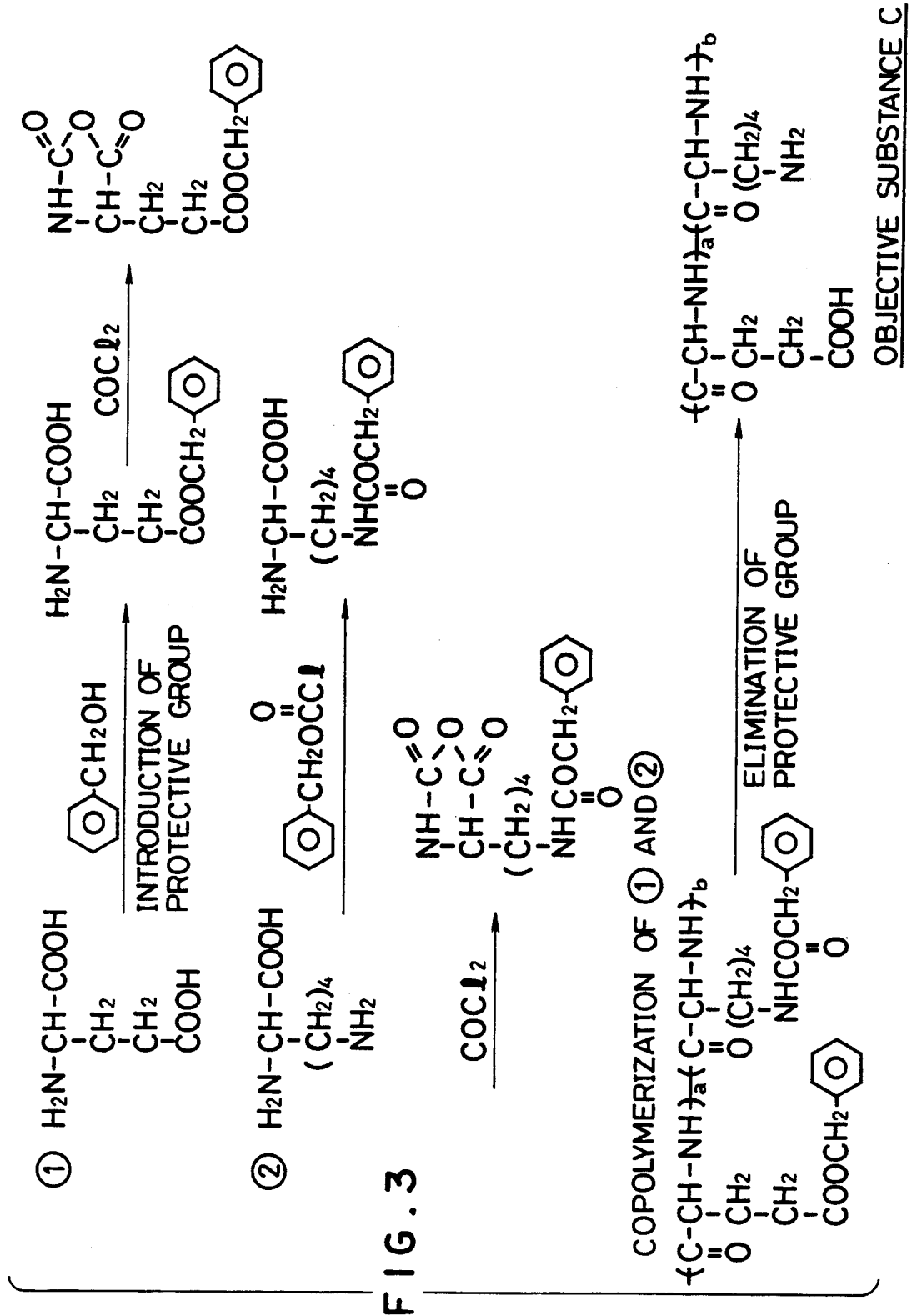
FIG. 3 also represents other reaction equations by which a synthetic polyamino acid of the present invention having at least one carboxyl group and at least one amino group is prepared.

(3) Copolymerization of an acidic amino acid and a basic amino acid:

The copolymerization can be carried out according to such reaction equation as shown in FIG. 3. As one example, FIG. 3 shows the copolymerization of glutamic acid and lysine, and a similar method can be applied to any case of use of other amino acids.

A copolymer of acidic polyamino acid and neutral polyamino acid, a copolymer of basic polyamino acid and neutral polyamino acid, and a copolymer of acidic polyamino acid, basic polyamino acid and neutral polyamino acid can also be used to prepare a polyamino acid having at least one carboxyl group and at least one amino group in its side chain for the present invention, through such procedures as set out in (1), (2) and (3) above, respectively.

The various process parameters for the methods (1) to (3) are well known in the art and are described in various publications. For example, where the introduction of amino group in the method (1) is carried out by use of ethylene diamine, hexamethylene diamine or the like as an amination agent, the diamine is added to polymer (a commercially available polymer is usable) in an appropriate ratio and these materials are reacted in water, preferably in distilled water, for 20 minutes to 2 hours under gradually increasing temperature, for example, at a reflux temperature, and the hydrolysis is carried out in the presence of an alkali such as NaOH, preferably under gradually increasing temperature, for 2 to 20 hours, preferably 5 to 15 hours. Since the polymer unit ratio of a to b (cf. FIG. 1 and 2), i.e., the ratio of COOH group to $NH_2$ group contained in the polymer can be changed to an appropriate value by adjusting the weight ratio of the starting polymer to the amination agent (for the method as shown in (1) above), the weight ratio of the starting polymer to the partial carboxylation agent (the method as shown in (2) above), or the ratio of the respective polymers for the copolymerization (the method as shown in (3) above), the present invention has advantages in that good coacervation is obtained in the coacervation process using the polyamino acid together with the anionic polymer so as to prepare the final carrier particles and that the sensitivity of the final carrier particles can be controlled according to the target antigen or antibody. In this connection, the ratio between COOH group and $NH_2$ group contained in the polymer is ordinarily 10:90 to 90:10, preferably 20:80 to 60:40. While amino acid has various polymerization degrees (n), n is ordinarily 50 to 1500, preferably 200 to 700.

As the anionic polymer which is another starting material for preparing the carrier particles, there can be used ones usable in the conventional coacervation method, for example, water soluble polysaccharides such as gum arabic, carboxymethyl cellulose, sodium alginate, agar, carrageenan and the like. In addition, there can be also used as the anionic polymer, for example, polyglutamic acid such as sodium polyglutamate, polyacrylate such as partially hydrolyzed polyacrylate and polyacrylamide. Preferred is gum arabic. Any of these commercially available is usable as the anionic polymer.

In order to obtain the desired carrier particles from the synthetic polyamino acid having at least one carboxyl group and at least one amino group in its side chain and the anionic polymer, this invention is based on the complex coacervation. Thus, the polyamino acid and the anionic polymer are used as polycation and polyanion, respectively, and thereby there is prepared a uniform aqueous solution within the range of concentrations at which coacervate occurs, the pH of the resulting solution is adjusted to not higher than the isoelectric point of the polyamino acid under stirring so as to obtain coacervate and the carrier particles can be prepared by insolubilizing the resulting coacervate. In more detail, a mixture of the polyamino acid and the anionic polymer having a weight ratio of about 5:1 to about 1:5, preferably about 2:1 to about 1:2, is dissolved in water, preferably distilled water, in a concentration of about 0.05 to 5 weight %, preferably about 0.1 to 3.0 weight % to obtain a solution with a pH of about 9 to 12. If necessary, insoluble materials can be removed therefrom by filtration or centrifugation. The pH of the solution is then adjusted to 3.0~9.0 by addition of an acid such as hydrochloric, sulfuric or acetic acid at room temperature or under gradually higher temperature (20°~40° C.), under stirring, to obtain coacervates, and the resulting coacervates are insolubilized by crosslinking them with a crosslinking agent. The pH range for forming the coacervates is determined in accordance with the ratio of COOH group to $NH_2$ group of amino acid used, the mixing ratio of the polyamino acid and the anionic polymer and the desired particle size. Therefore, according to this invention, properties and particles size of the thus obtained paricles can be optionally controlled. For example, particles of large particle size can be prepared by lowering the pH while particles of small particle size can be prepared by raising the pH, and thereby, the particle size of the particles can be controlled to 2~10 μm, which is suitable for use in microtiter plate agglutination reaction or to 0.1~1.0 μm which is suitable for use in latex agglutination reaction. The thus-prepared particles have an electric double layer similar to that of animal erythrocytes and thus have stable dispersability and good agglutination properties at the time of conducting the assay.

Examples of aldehyde crosslinking agent usable for insolubilizing the particles include ordinary ones usable in the crosslinking of the coacervate, for example, glutaraldehyde, formaldehyde, glyoxal, crotonyl aldehyde, acrolein, acetoaldehyde and the like, the preferred one being glutaraldehyde. The crosslinking agent is added in an amount of about 0.01 to 5.0 weight %, preferably 0.1 to 2.0 weight %, to the aqueous solution after formation of the coacervate.

In this invention, a part of the synthetic amino acid polymer can be replaced with an optional polycationic ingredient such as gelatin while a part of the anionic polymer can be replaced with an optional polyanionic ingredient such as sodium polyphosphate. Furthermore, animal erythrocytes or other suitable core materials can be present in the coacervate preparation to obtain capsule particles. In this case, since the surface (capsule membrane) of the particles consists of the synthetic amino acid and the anionic polymer, there can be prepared carrier particles which are substantially identical with those described above.

Furthermore, in accordance with necessity, it is possible to use an ordinary polar solvent such as methanol, ethanol or acetone as a insolubilizing solvent at the time of the coacervation granulation for the purpose of accelerating the production of the coacervate (production of the particles) and to use a surfactant, in particular, an anionic surfactant or a nonionic surfactant for the purpose of improving the disparsability of the thus prepared particles. Although these polar solvents and/or surfactants are used in an amount effective for the purpose, it is sufficient that the former be used in an amount of 5 to 60 weight % of the solution for forming the coacervate and the latter be used in an amount of 0.005 to 0.5 weight %.

Although the thus obtained carrier particles of this invention are substantially colorless, the particles can, if desired, be colored by a conventional method with an ordinary dye, for example, a reactive dye such as reactive red 4, reactive red 120, reactive blue 4, or reactive red 5, or a direct dye such as direct orange 31, direct red 31 or direct blue. Specifically, the thus prepared insoluble polyamino acid particles are immersed for one night in a solution of appropriate concentration for dying, for example, in a solution containing the dye in an amount of 0.01 to 3.0%. Alternatively, the dye can be added to the solution for forming the particles.

Sensitization of an antigen or an antibody to the particles of this invention can be easily carried out by the conventional method for adsorbing it to animal erythrocytes. For example, the particles are conventionally subjected to tannic acid treatment, after which desired antigen or antibody is adsorbed thereon. The antigen or antibody for use in the sensitization may be an optional one from a natural source or from a product of gene recombination, cell fusion or chemical synthesis, which corresponds to the one to be analyzed.

As shown by the following examples, the sensitized carrier of this invention has properties similar to those of conventional animal erythrocytes and gelatin carriers and also has novel characteristics in that the sedimentation rate after the agglutination is high, so that it is possible to shorten the time period for the assay. Although the reason for their high sedimentation rate is not clear, it is estimated that it is related to the specific gravity of the carrier particles of this invention because the specific gravity of the carrier particles of this invention is larger than that of animal erythrocytes or gelatin.

The present invention and characteristic thereof are explained with reference to the following non-limitative examples.

Referential Example 1

Preparation of polyglutamic acid to which an amino group is introduced.

According to the conventional method, powders of poly-γ-methyl-L-glutamate were prepared by reprecipitating from methanol Ajicoat A-2000 (which is a 10 weight % solution of poly-γ-methyl-L-glutamate, the polymerization degree being about 580, and is commercially available from Ajinomoto Co. Ltd.) and drying the resulting material. 70 g of the resulting powders were charged in a 2 l flask provided with a condenser, thermometer and stirrer, which contained therein ethylene diamine and distilled water in a ratio listed in Table 1, and were heated at the reflux temperature for about 1 hour. 350 ml of 2 weight % NaOH aqueous solution was then added thereto and the reaction was continued until the reaction solution became substantially transparent, after which 14 g of solid NaOH was added thereto. The resultant was directly subjected to suction filtration using a cotton cloth to remove an insoluble material therefrom and further concentrated by a vacuum evaporator to remove water and residual ethylenediamine, whereby about 200 ml of viscous material was obtained. The viscous material was dissolved in about 0.7 to 1 l of ethanol and the resulting solution was added to 2 to 3 l of ether to prepare flake materials. The materials were filtrated by suction, washed with an appropriate amount of a mixture of ethanol and ether in a ratio of 1:3 and an appropriate amount of ether in this order, and dried under vacuum to obtain each sample in an amount of about 50 to 70 g.

TABLE 1

| Sample No. | Ethylenediamine | Water |
|---|---|---|
| 1 | 500 ml | 500 ml |
| 2 | 600 ml | 400 ml |
| 3 | 700 ml | 300 ml |
| 4 | 800 ml | 200 ml |
| 5 | 300 ml | 700 ml |
| 6 | 400 ml | 600 ml |

Another sample, Sample 7, was also prepared without addition of ethylenediamine, i.e., the hydrolysis was only conducted until the reaction solution became transparent.

Regarding these Samples 1 to 7, viscosity of 1M-acetic acid aqueous solution containing the sample in an amount of 0.01 g/1 ml was measured and ratio of COOH group to $NH_2$ group (a:b) was also determined by NMR spectroanalysis. The results obtained are shown in Table 2.

TABLE 2

| Sample No. | Viscosity (cp) | a:b |
|---|---|---|
| 1 | 1,330 | 51:49 |
| 2 | 1,305 | 39:61 |
| 3 | 1,306 | 31:69 |
| 4 | 1,308 | 12:88 |
| 5 | 1,308 | 73:27 |
| 6 | 1,296 | 60:40 |
| 7 | 1,256 | 100:0 |

Referential Example 2

Preparation of poly-L-lysine to which a carboxylic group is introduced.

10 g of poly (L-lysine) bromate (which is available from Seikagaku Kogyo K. K. and has a polymerization degree of about 300) and 14 ml of triethylamine were added to 100 ml of dimethylformamide and stirred at a room temperature for 1 hour, after which 2.7 g of succinic anhydride was added thereto. After stirring at room temperature for 6 hours and further stirring at a temperature of 60° C. for 1 hour, the solution was concentrated to 20 ml by an evaporator. 100 ml of ethanol in which 3.8 g of NaOH was dissolved was added to the resulting concentrate, sufficiently mixed therewith by shaking, after which the resultant was left to stand in a refrigerator for one night. The solid was collected by filtration, sufficiently washed with ether and dried. 7.6 g of the desired polymer was obtained (yield was 90% as sodium salt of the polymer) and the ratio of amino group to carboxyl group was determined to be about 60:40 by NMR spectroanalysis. The thus obtained polymer was used as Sample 8.

Referential Example 3

Preparation of poly-L-glutamic acid and poly-L-lysine copolymer 30.6 g of $N^\epsilon$-carbobenzoxy-L-lysine $N^\alpha$-carboxy anhydride prepared by the conventional method (phosgene method) and 26.3 g of γ-benzyl-L-glutamic N-carboxy anhydride were dissolved in 600 ml of tetrahydrofuran.

0.15 ml of triethylamine as polymerization initiator was added thereto under stirring at a room temperature. After stirring for two days, the solution was concentrated to 100 ml under vacuum by an evaporator and 1000 ml of water was added thereto to obtain white precipitates. The precipitates were washed with methanol and water, and dried. 43.3 g of the copolymer was obtained at a yield of 90% as 1:1 copolymer. The thus obtained copolymer was dissolved in 200 ml of mixed solution of trifluoroacetic acid and hydrobromic acid, stirred at room temperature for 1 hour, after which 500 ml of ether was added thereto to obtain yellow brown precipitates. The precipitates were collected by filtration, sufficiently washed with ethanol and ether, and dried to obtain 27.5 g of the desired copolymer (yield was 85% based on the starting material). In this case, it was confirmed by NMR spectralanalysis that the residual lysine of the thus obtained copolymer was formed as hydrobromate and that the ratio of lysine to glutamic acid was 50:50. The resultant copolymer was further dissolved in water and treated with NaOH to prepare Na salt thereof. After reprecipitating from ether, the resultant copolymer (Sample 9) was used in the latter process of coacervation.

EXAMPLE 1

Preparation of carrier particles

Granulation of Samples 1 to 9 prepared in Referential Examples 1 to 3 was carried out by the following method:

(1) In case of Samples 1 to 3, 6, 8 and 9:

1.0 g of each sample, 20 ml of 5% gum arabic aqueous solution and 180 ml of distilled water were sufficiently mixed in a beaker and 1.5 ml of 2 weight % active red 120 aqueous solution was added thereto to prepare each stock solution. The PH of the stock solution was controlled with 10 weight % acetic acid solution at room temperature under sufficient stirring, and the formation and the particle diameter of the solution drops (coacervates) were checked by an optical microscope. 2.5 ml of 25 weight % glutaraldehyde (GA) aqueous solution was then added thereto and aggitated at room temperature for about 1 hour followed by further aggitation at a temperature of about 40° C. for about 1 hour. The resulting particles were sufficiently washed with distilled water three times. Centrifugal separation (for 5 minutes at 2000 rpm) was used to recover the residue. The PH of each stock solution relative to each Sample and the pH of the solution when the coacervates having the desired particle diameter were formed are shown in Table 3.

TABLE 3

| Sample No. | PH of the stock solution | PH of the solution when the coacervates were formed |
|---|---|---|
| 1 | 10.92 | 5.63 |
| 2 | 11.02 | 7.56 |
| 3 | 11.58 | 8.18 |
| 6 | 10.97 | 4.57 |
| 8 | 11.05 | 7.50 |
| 9 | 10.95 | 6.01 |

Figure 4:
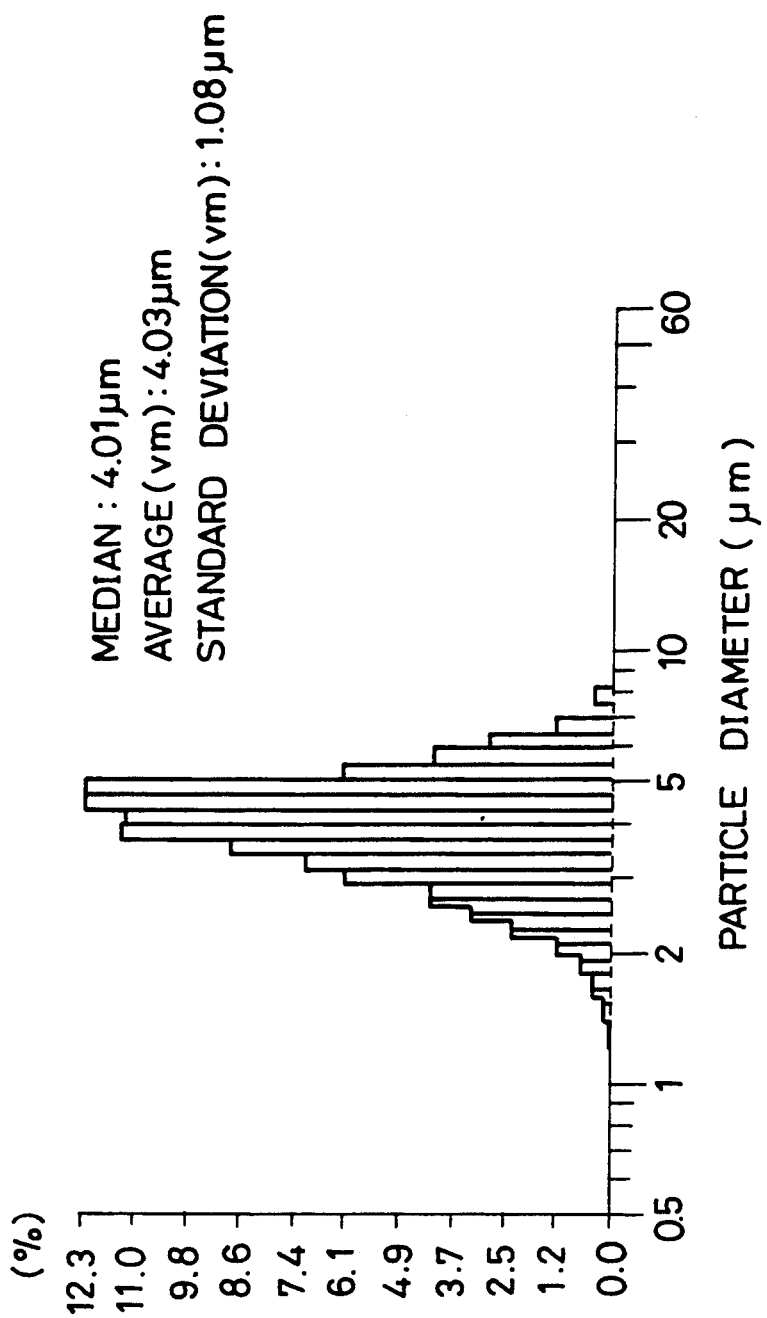
FIG. 4 is a histogram showing the particle diameter distribution (volume distribution) of the carrier particles of FIG. 1.
Figure 5:
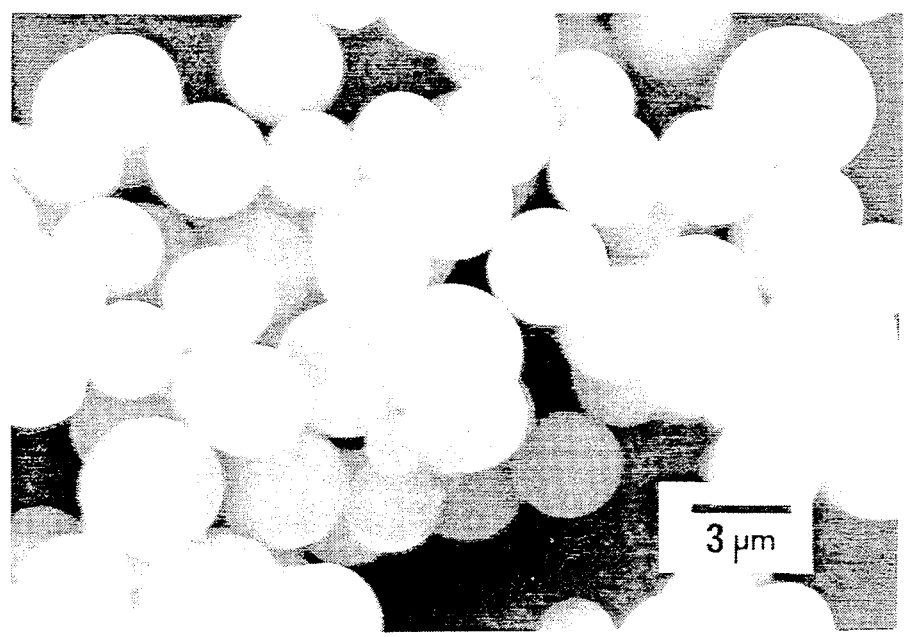
FIG. 5 is a photograph showing the structure of the carrier particles of the present invention (Sample 2).

The ratio of particles in the range of 2 to 7 $\mu$m contained in each Sample was determined by a particle size distribution analyzer available from Galai Co. Ltd. In each case the ratio was found to be in the range of 93 to 94% (volume distribution). A histogram and a microscopic photograph of Sample 2 are shown in FIGS. 4 and 5.

The degree of the electrophoresis of each carrier particles of the Samples set out above was determined with a system 3000 Automated Electrokinetics Analyzer manufactured by PENKEM, Inc. For this, the particles were suspended in a solution containing 0.15M PBS and having a PH of 7.2 and the suspension was charged in a 1 mm$\Phi \times$20 mm cylindrical electrophoresis cell to measure the degree of electrophoresis under the gradient voltage of 1048 V/m at room temperature. It was found that the degree of electrophoresis of each particle was in the range of $-0.87$ to $-1.20$ $\mu$m/sec/V/cm and that the degree was the same as $-1.15$ $\mu$m/sec/V/cm of sheep erythrocytes and $-0.75$ to $-1.85$ $\mu$m/sec/V/cm of gelatin particles determined in a manner similar to that of the method set out above, which data were reported in publications such as Rinshokensa Vol. 30 No. 13, 1709-1710 and Japanese Patent Unexamined Publication No. 57-153658.

Furthermore, the specific gravity of each particle was determined by the following method. First, sucrose solutions of 20 w/w %, 30 w/w %, 40 w/w %, 50 w/w %, 60 w/w % and 65 w/w % were prepared and 2 ml of the respective solutions were charged in a test tube in the order of their weight, with the heaviest one being charged first. 0.5 ml of 1% carrier particle floating solution was added to the upper most layer of the sucrose solution of 20 w/w %. The test tube was then subjected to centrifugal separation at 3000 rpm for 20 minutes. After centrifugation, all carrier particles were found to be present in the sucrose solutions of 60 w/w % and 65 w/w %. The same experiment was conducted for sheep fixed erythrocytes, in which case the erythrocytes were found to be present in the sucrose solutions of 60 w/w % and 50 w/w %. This result shows that the polyamino acid carrier particles have a higher specific gravity than that of the sheep fixed erythrocytes which are similar to those of gelatin particles.

(2) In case of Sample 4:

Carrier particles having a particle size distribution substantially the same as that of the particles of item (1) were prepared by the same granulation method as that of item (1) except that the amino acid sample was used in an amount of 0.5 g.

| | |
|---|---|
| PH of stock solution | 11.36 |
| PH of the solution for forming the desired particle diameter | 9.23 |

(3). In case of Sample 5:

Carrier particles having the particle diameter distribution substantially the same as that of the particles of item (1) were prepared by the same granulation method as that of item (1) except that a mixture of 100 ml of water and 80 ml of ethanol was used instead of 180 ml of water.

| | |
|---|---|
| PH of stock solution | 10.97 |
| PH of the solution for forming the desired particle diameter | 5.86 |

(4) In case of Sample 7:

Conditions such as PH and amount of added insolubilizing solvent were variously changed, but the desired particles could not be formed.

(5) In case of Sample 10:

Carrier particles having a particle diameter distribution substantially the same as that of the particles of item (1) were prepared by the same granulation method as that of item (1) except that an aqueous solution containing sodium polyglutamate (MW: 7200) was used instead of 5% gum arabic aqueous solution.

(6) In case of Samples 11 and 12:

Carrier particles comprising a copolymer of glutamic acid and leucine and having a particle size distribution substantially the same as that of the particles of item (1) were prepared by the same granulation method as that of item (1) except that the following raw materials were used.

| | | |
|---|---|---|
| Glutamic acid | 98 mol % | 95 mol % |
| Leucine | 2 mol % | 5 mol % |
| Ratio of amino acid group to carboxy group | 65:35 | 56:44 |
| PH of stock solution | 11.14 | 11.32 |
| PH of the solution for forming the desired particle size | 6.52 | 7.01 |

EXAMPLE 2

Preparation of carrier particles

In the granulation method of item (1), Sample 2 was used without addition of the dye and glutal aldehyde was added to the solution when the PH of the solution reached 7.91, followed by centrifugal separation at 2500 rpm for 10 minutes to collect a supernatant liquid. The collected supernatant was filtrated using a 1 μm membrane filter and the filtrate was subjected to centrifugal separation at 4000 rpm for 10 minutes to obtain particles. The particle size of the thus obtained particles was determined by a particle diameter distribution analyzer CIS-1 manufactured by Galai Co. Ltd. As a result, it was found that about 80% of the particles had a particle diameter in the range of 0.5 to 1.0 μm (volume distribution). These particles are usable as particles in latex agglutinaion such as the Turbidimetric immunoassay.

EXAMPLE 3

With carrier particles of the present invention as prepared by the method in Example 1, as well as sheep-fixed erythrocytes as reference, particle agglutination tests were done by the conventional microtiter method. For the tests, the carrier particles (and the sheep-fixed erythrocytes) were subjected to a conventional sensitization treatment with tannic acid, and then sensitized (coated) with the adsorbing materials (antigens or antibodies) as shown in Table 4. The specimens for testing are human sera which are positive or negative with respect to the components corresponding to the respective adsorbing antigens or antibodies. Thus, for example, in the case of the test of HBs antigen sensitized carrier, anti-HBs antibody positive human serum was used as positive specimen and anti-HBs antibody negative human serum was used as negative specimen. The exception was the use of anti-BSA rabbit immune serum as positive specimen for the bovine serum albumin (BSA) sensitized carriers.

The tests were carried out firstly by adding 25 μl of diluent to each well of the microtiter plate. Then, 25 μl of each specimen was serially diluted (through the two-fold dilutions) in the wells, and mixed with 25 μl of 1 v/v % suspension of the sensitized carrier particles (or the sensitized sheep-fixed erythrocytes as reference). The mixture was allowed to stand for two hours at room temperature. The highest dilution giving a positive reaction (agglutination reaction) was determined to be the endpoint (agglutination titer).

The condition for the sensitizations as described above was as follows:

One milliliter of 2.5% suspension (in PBS, pH 7.2) of the carrier particles (or the sheep fixed erythrocytes) was mixed with an equal volume of tannic acid solution (in PBS) and the mixture was allowed to stand for 30 min. at 37° C. After removal of supernatant with centrifugation, the particles were washed with PBS, and then suspended in 1 ml of PBS. One milliliter containing each amount of antigen (or antibody) source was added to each preparation and then incubated at 37° C. for 30 min. After the incubation, supernatant was removed by centrifugation. The particles were washed with PBS 3 times, and suspended in 2.5 ml of PBS. A 1% concentration by volume of sensitized particles was used for testing.

Results obtained are shown in Table 4. As is clear from the data of Table 4, it is understood that the carrier particles of this invention have an endpoint equal or superior to that of sheep fixed erythrocytes. In addition, it was possible that the assay was finished from about 60 to 80 minutes by use of the carrier particle of this invention, while the sheep fixed erythrocytes required about 90 to 120 minutes to finish the assay.

TABLE 4

| | | End point | |
|---|---|---|---|
| Sensitizing material | Carrier | Positive specimen | negative specimen |
| HBc antigen (from recombinant yeast) | Sheep fixed erythrocytes | $2^9$ | $<2^1$ |
| | carrier particles of Sample 1 | $2^{18}$ | $<2^1$ |
| HBs antigen (from plasma) | Sheep fixed erythrocytes | $2^7$ | $<2^1$ |
| | carrier particles of Sample 3 | $2^7$ | $<2^1$ |
| HBs antigen (from recombinant yeast) | Sheep fixed erythrocytes | $2^7$ | $<2^1$ |
| | carrier particles of Sample 3 | $2^7$ | $<2^1$ |
| HBs antibody (guinea pig) | Sheep fixed erythrocytes | $2^8$ | $<2^1$ |
| | carrier particles of Sample 2 | $2^8$ | $<2^1$ |
| HBs antibody (mouse monoclonal) | Sheep fixed erythrocytes | $2^8$ | $<2^1$ |
| | carrier particles of Sample 2 | $2^9$ | $<2^1$ |
| HIV antigen *1 | Sheep fixed erythrocytes | $2^8$ | $<2^1$ |
| | carrier particles of Sample 2 | $2^8$ | $<2^1$ |
| Bovine serum albumin | Sheep fixed erythrocytes | $2^{10}$ | $<2^1$ |
| | carrier particles of Sample 8 | $2^{10}$ | $<2^1$ |

*1 This antigen eas solubilized with a surfactant by the conventional method.

What is claimed is:

1. An artificial carrier particle, comprising;
    a complex of (A) a synthetic polyamino acid having at least one carboxylic group and at least one amino group in its side chain, in which a molar ratio of the carboxyl group to the amino group is about 10:90 to about 90:10 and a polymerization degree of 50 to 1500; and
    (B) an anionic polymer selected from the group consisting of water soluble polysaccharides, polyglutamate and polyacrylate, the complex being insolubilized by an aldehyde crosslinking agent selected from the group consisting of glutaraldehyde, formaldehyde, glyoxal, crotonyl aldehyde, acrolein and acetoaldehyde.

2. The artificial carrier particle of claim 1, wherein the synthetic polyamino acid is an acidic polyamino acid and the amino group is introduced in the acidic polyamino acid via a part of a free carboxyl group of the polyamino acid.

3. The artificial carrier particle of claim 1, wherein the synthetic polyamino acid is a basic polyamino acid and the carboxyl group is introduced in the basic polyamino acid via a part of a free amino group of the polyamino acid.

4. The artificial carrier particle of claim 1, wherein the synthetic polyamino acid is a copolymer of an acidic polyamino acid and a basic polyamino acid.

5. The artificial carrier particle of claim 1, wherein a weight ratio of the synthetic polyamino acid to the anionic polymer is about 5:1 to about 1:5.

6. The artificial carrier particle of claim 5, wherein a weight ratio of the synthetic polyamino acid to the anionic polymer is about 2:1 to about 1:2.

7. The artificial carrier particle of claim 1, wherein the molar ratio of the carboxyl group to the amino group of the synthetic polyamino acid (A) is about 20:80 to about 60:40.

8. The artificial carrier particle of claim 1, wherein the water soluble polysaccharides are selected from the group consisting of gum arabic, carboxymethyl cellulose, sodium alginate, agar and carrageenan, wherein further the polyglutamate is sodium polyglutamate, and wherein further the polyacrylate is selected from the group of partially hydrolyzed polyacrylate and polyacryl amide.

* * * * *